United States Patent
Baker, Jr.

(10) Patent No.: US 8,092,379 B2
(45) Date of Patent: Jan. 10, 2012

(54) METHOD AND SYSTEM FOR DETERMINING WHEN TO REPOSITION A PHYSIOLOGICAL SENSOR

(75) Inventor: Clark R. Baker, Jr., Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 541 days.

(21) Appl. No.: 11/240,441

(22) Filed: Sep. 29, 2005

(65) Prior Publication Data

US 2007/0068527 A1 Mar. 29, 2007

(51) Int. Cl.
*A61B 5/00* (2006.01)

(52) U.S. Cl. ........ 600/300; 600/301; 600/323; 600/324; 128/905; 128/920

(58) Field of Classification Search .................. 600/300, 600/301; 128/903–905, 920
See application file for complete search history.

(56) References Cited

U.S. PATENT DOCUMENTS

| | | | |
|---|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |

(Continued)

FOREIGN PATENT DOCUMENTS

JP 2237544 9/1990

(Continued)

OTHER PUBLICATIONS

Skin Integrity Issues Associated with Pulse Oximetry. PA-PSPS Patient Safety Advisory, vol. 2, No. 2—Jun. 2005.*

(Continued)

*Primary Examiner* — Sam Yao
*Assistant Examiner* — Bobby Soriano

(57) ABSTRACT

A sensor may be placed on a patient to obtain physiological measurements. The application of the sensor on the patient may start a timer set to run for a given time interval. If the sensor is repositioned before the interval is expired, the timer is reset. If the time expires without the sensor being repositioned, a caregiver is prompted to reposition the sensor.

52 Claims, 2 Drawing Sheets

U.S. PATENT DOCUMENTS

| | | |
|---|---|---|
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |

| Patent No. | Date | Inventor(s) |
|---|---|---|
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,583,832 A | 12/1996 | DePonty |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,691,932 A | 11/1997 | Reiner et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |

| | | | | | | |
|---|---|---|---|---|---|---|
| 5,934,277 A | 8/1999 | Mortz | | 6,198,951 B1 | 3/2001 | Kosuda et al. |
| 5,934,925 A | 8/1999 | Tobler et al. | | 6,206,830 B1 | 3/2001 | Diab et al. |
| 5,940,182 A | 8/1999 | Lepper, Jr. et al. | | 6,213,952 B1 | 4/2001 | Finarov et al. |
| 5,954,644 A | 9/1999 | Dettling et al. | | 6,217,523 B1 | 4/2001 | Amano et al. |
| 5,960,610 A | 10/1999 | Levinson et al. | | 6,222,189 B1 | 4/2001 | Misner et al. |
| 5,961,450 A | 10/1999 | Merchant et al. | | 6,226,539 B1 | 5/2001 | Potratz |
| 5,961,452 A | 10/1999 | Chung et al. | | 6,226,540 B1 | 5/2001 | Bernreuter et al. |
| 5,964,701 A | 10/1999 | Asada et al. | | 6,229,856 B1 | 5/2001 | Diab et al. |
| 5,971,930 A | 10/1999 | Elghazzawi | | 6,230,035 B1 | 5/2001 | Aoyagi et al. |
| 5,978,691 A | 11/1999 | Mills | | 6,233,470 B1 | 5/2001 | Tsuchiya |
| 5,978,693 A | 11/1999 | Hamilton et al. | | 6,236,871 B1 | 5/2001 | Tsuchiya |
| 5,983,122 A | 11/1999 | Jarman et al. | | 6,236,872 B1 | 5/2001 | Diab et al. |
| 5,987,343 A | 11/1999 | Kinast | | 6,240,305 B1 | 5/2001 | Tsuchiya |
| 5,991,648 A | 11/1999 | Levin | | 6,253,097 B1 | 6/2001 | Aronow et al. |
| 5,995,855 A | 11/1999 | Kiani et al. | | 6,253,098 B1 | 6/2001 | Walker et al. |
| 5,995,856 A | 11/1999 | Mannheimer et al. | | 6,256,523 B1 | 7/2001 | Diab et al. |
| 5,995,858 A | 11/1999 | Kinast | | 6,256,524 B1 | 7/2001 | Walker et al. |
| 5,995,859 A | 11/1999 | Takahashi | | 6,261,236 B1 | 7/2001 | Grimblatov |
| 5,997,343 A | 12/1999 | Mills et al. | | 6,263,221 B1 | 7/2001 | Chance et al. |
| 5,999,834 A | 12/1999 | Wang et al. | | 6,263,222 B1 | 7/2001 | Diab et al. |
| 6,002,952 A | 12/1999 | Diab et al. | | 6,263,223 B1 | 7/2001 | Sheperd et al. |
| 6,005,658 A | 12/1999 | Kaluza et al. | | 6,266,546 B1 | 7/2001 | Steuer et al. |
| 6,006,120 A | 12/1999 | Levin | | 6,266,547 B1 | 7/2001 | Walker et al. |
| 6,011,985 A | 1/2000 | Athan et al. | | 6,272,363 B1 | 8/2001 | Casciani et al. |
| 6,011,986 A | 1/2000 | Diab et al. | | 6,278,522 B1 | 8/2001 | Lepper, Jr. et al. |
| 6,014,346 A | 1/2000 | Malone | | 6,280,213 B1 | 8/2001 | Tobler et al. |
| 6,014,576 A | 1/2000 | Raley et al. | | 6,280,381 B1 | 8/2001 | Malin et al. |
| 6,018,673 A | 1/2000 | Chin et al. | | 6,285,894 B1 | 9/2001 | Oppelt et al. |
| 6,018,674 A | 1/2000 | Aronow | | 6,285,895 B1 | 9/2001 | Ristolainen et al. |
| 6,022,321 A | 2/2000 | Amano et al. | | 6,285,896 B1 | 9/2001 | Tobler et al. |
| 6,023,541 A | 2/2000 | Merchant et al. | | 6,298,252 B1 | 10/2001 | Kovach et al. |
| 6,026,312 A | 2/2000 | Shemwell et al. | | 6,308,089 B1 | 10/2001 | Von der Ruhr et al. |
| 6,026,314 A | 2/2000 | Amerov et al. | | 6,321,100 B1 | 11/2001 | Parker |
| 6,031,603 A | 2/2000 | Fine et al. | | 6,330,468 B1 | 12/2001 | Scharf |
| 6,035,223 A | 3/2000 | Baker, Jr. | | 6,334,065 B1 | 12/2001 | Al-Ali et al. |
| 6,036,642 A | 3/2000 | Diab et al. | | 6,339,715 B1 | 1/2002 | Bahr et al. |
| 6,041,247 A | 3/2000 | Weckstrom et al. | | 6,343,223 B1 | 1/2002 | Chin et al. |
| 6,044,283 A | 3/2000 | Fein et al. | | 6,343,224 B1 | 1/2002 | Parker |
| 6,047,201 A | 4/2000 | Jackson, III | | 6,349,228 B1 | 2/2002 | Kiani et al. |
| 6,061,584 A | 5/2000 | Lovejoy et al. | | 6,351,658 B1 | 2/2002 | Middleman et al. |
| 6,064,898 A | 5/2000 | Aldrich | | 6,353,750 B1 | 3/2002 | Kimura et al. |
| 6,064,899 A | 5/2000 | Fein et al. | | 6,356,774 B1 | 3/2002 | Bernstein et al. |
| 6,067,462 A | 5/2000 | Diab et al. | | 6,360,113 B1 | 3/2002 | Dettling |
| 6,073,038 A | 6/2000 | Wang et al. | | 6,360,114 B1 | 3/2002 | Diab et al. |
| 6,078,833 A | 6/2000 | Hueber | | 6,361,501 B1 | 3/2002 | Amano et al. |
| 6,081,735 A | 6/2000 | Diab et al. | | 6,363,269 B1 | 3/2002 | Hanna et al. |
| 6,081,742 A | 6/2000 | Amano et al. | | 6,370,408 B1 | 4/2002 | Merchant et al. |
| 6,083,157 A | 7/2000 | Noller | | 6,370,409 B1 | 4/2002 | Chung et al. |
| 6,083,172 A | 7/2000 | Baker, Jr. et al. | | 6,374,129 B1 | 4/2002 | Chin et al. |
| 6,088,607 A | 7/2000 | Diab et al. | | 6,377,829 B1 | 4/2002 | Al-Ali et al. |
| 6,094,592 A | 7/2000 | Yorkey et al. | | 6,381,479 B1 | 4/2002 | Norris |
| 6,095,974 A | 8/2000 | Shemwell et al. | | 6,381,480 B1 | 4/2002 | Stoddar et al. |
| 6,104,938 A | 8/2000 | Huiku et al. | | 6,385,471 B1 | 5/2002 | Mortz |
| 6,112,107 A | 8/2000 | Hannula | | 6,385,821 B1 | 5/2002 | Modgil et al. |
| 6,113,541 A | 9/2000 | Dias et al. | | 6,388,240 B2 | 5/2002 | Schulz et al. |
| 6,115,621 A | 9/2000 | Chin | | 6,393,310 B1 | 5/2002 | Kuenster |
| 6,122,535 A | 9/2000 | Kaestle et al. | | 6,397,091 B2 | 5/2002 | Diab et al. |
| 6,133,994 A | 10/2000 | Mathews et al. | | 6,397,092 B1 | 5/2002 | Norris et al. |
| 6,135,952 A | 10/2000 | Coetzee | | 6,397,093 B1 | 5/2002 | Aldrich |
| 6,144,444 A | 11/2000 | Haworth et al. | | 6,398,727 B1 | 6/2002 | Bui et al. |
| 6,144,867 A | 11/2000 | Walker et al. | | 6,400,971 B1 | 6/2002 | Finarov et al. |
| 6,144,868 A | 11/2000 | Parker | | 6,400,972 B1 | 6/2002 | Fine |
| 6,149,481 A | 11/2000 | Wang et al. | | 6,402,690 B1 | 6/2002 | Rhee et al. |
| 6,150,951 A | 11/2000 | Olejniczak | | 6,408,198 B1 | 6/2002 | Hanna et al. |
| 6,151,107 A | 11/2000 | Schöllermann et al. | | 6,411,832 B1 | 6/2002 | Guthermann |
| 6,151,518 A | 11/2000 | Hayashi | | 6,411,833 B1 | 6/2002 | Baker, Jr. et al. |
| 6,152,754 A | 11/2000 | Gerhardt et al. | | 6,419,671 B1 | 7/2002 | Lemberg |
| 6,154,667 A | 11/2000 | Miura et al. | | 6,421,549 B1 | 7/2002 | Jacques |
| 6,157,850 A | 12/2000 | Diab et al. | | 6,430,423 B2 | 8/2002 | DeLonzor et al. |
| 6,163,715 A | 12/2000 | Larsen et al. | | 6,430,513 B1 | 8/2002 | Wang et al. |
| 6,165,005 A | 12/2000 | Mills et al. | | 6,430,525 B1 | 8/2002 | Weber et al. |
| 6,173,196 B1 | 1/2001 | Delonzor et al. | | 6,434,408 B1 | 8/2002 | Heckel et al. |
| 6,178,343 B1 | 1/2001 | Bindszus et al. | | 6,438,399 B1 | 8/2002 | Kurth |
| 6,181,958 B1 | 1/2001 | Steuer et al. | | 6,449,501 B1 | 9/2002 | Reuss |
| 6,181,959 B1 | 1/2001 | Schöllermann et al. | | 6,453,183 B1 | 9/2002 | Walker |
| 6,184,521 B1 | 2/2001 | Coffin, IV et al. | | 6,453,184 B1 | 9/2002 | Hyogo et al. |
| 6,188,470 B1 | 2/2001 | Grace | | 6,456,862 B2 | 9/2002 | Benni |
| 6,192,260 B1 | 2/2001 | Chance | | 6,461,305 B1 | 10/2002 | Schnall |
| 6,195,575 B1 | 2/2001 | Levinson | | 6,463,310 B1 | 10/2002 | Swedlow et al. |

| | | |
|---|---|---|
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B1 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,579,242 B2 | 6/2003 | Bui et al. |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,549 B2 | 12/2004 | Bui |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |

| | | | | | | |
|---|---|---|---|---|---|---|
| 6,845,256 B2 | 1/2005 | Chin et al. | | 7,263,395 B2 | 8/2007 | Chan et al. |
| 6,850,787 B2 | 2/2005 | Weber et al. | | 7,272,426 B2 | 9/2007 | Scmid |
| 6,850,788 B2 | 2/2005 | Al-Ali | | 7,280,858 B2 | 10/2007 | Al-Ali et al. |
| 6,850,789 B2 | 2/2005 | Schweitzer, Jr. et al. | | 7,295,866 B2 | 11/2007 | Al-Ali et al. |
| 6,861,639 B2 | 3/2005 | Al-Ali | | 7,305,262 B2 | 12/2007 | Brodnick et al. |
| 6,863,652 B2 | 3/2005 | Huang et al. | | 7,315,753 B2 | 1/2008 | Baker, Jr. et al. |
| 6,865,407 B2 | 3/2005 | Kimball et al. | | 7,415,297 B2 | 8/2008 | Ali Ali et al. |
| 6,879,850 B2 | 4/2005 | Kimball | | 2001/0021803 A1 | 9/2001 | Blank et al. |
| 6,882,874 B2 | 4/2005 | Huiku | | 2001/0045509 A1 | 11/2001 | Al-Ali |
| 6,889,153 B2 | 5/2005 | Dietiker | | 2001/0051767 A1 | 12/2001 | Williams et al. |
| 6,898,452 B2 | 5/2005 | Al-Ali et al. | | 2002/0026109 A1 | 2/2002 | Diab et al. |
| 6,909,912 B2 | 6/2005 | Melker et al. | | 2002/0028990 A1 | 3/2002 | Sheperd et al. |
| 6,912,413 B2 | 6/2005 | Rantala et al. | | 2002/0038078 A1 | 3/2002 | Ito |
| 6,916,289 B2 | 7/2005 | Schnall | | 2002/0042558 A1 | 4/2002 | Mendelson |
| 6,920,345 B2 | 7/2005 | Al-Ali et al. | | 2002/0068859 A1 | 6/2002 | Knopp |
| 6,931,269 B2 | 8/2005 | Terry | | 2002/0128544 A1 | 9/2002 | Diab et al. |
| 6,934,570 B2 | 8/2005 | Kiani et al. | | 2002/0133067 A1 | 9/2002 | Jackson, III |
| 6,939,307 B1 | 9/2005 | Dunlop | | 2002/0156354 A1 | 10/2002 | Larson |
| 6,941,162 B2 | 9/2005 | Fudge et al. | | 2002/0173706 A1 | 11/2002 | Takatani |
| 6,947,781 B2 | 9/2005 | Asada et al. | | 2002/0173709 A1 | 11/2002 | Fine et al. |
| 6,950,687 B2 | 9/2005 | Al-Ali | | 2002/0190863 A1 | 12/2002 | Lynn |
| 6,963,767 B2 | 11/2005 | Rantala et al. | | 2002/0198442 A1 | 12/2002 | Rantala et al. |
| 6,971,580 B2 | 12/2005 | Zhu et al. | | 2003/0018243 A1 | 1/2003 | Gerhardt et al. |
| 6,979,812 B2 | 12/2005 | Al-Ali | | 2003/0036690 A1 | 2/2003 | Geddes et al. |
| 6,983,178 B2 | 1/2006 | Fine et al. | | 2003/0045785 A1 | 3/2003 | Diab et al. |
| 6,985,763 B2 | 1/2006 | Boas et al. | | 2003/0073889 A1 | 4/2003 | Keilbach et al. |
| 6,985,764 B2 | 1/2006 | Mason et al. | | 2003/0073890 A1 | 4/2003 | Hanna |
| 6,990,426 B2 | 1/2006 | Yoon et al. | | 2003/0100840 A1 | 5/2003 | Sugiura et al. |
| 6,992,751 B2 | 1/2006 | Okita et al. | | 2003/0132495 A1 | 7/2003 | Mills et al. |
| 6,992,772 B2 | 1/2006 | Block et al. | | 2003/0135099 A1 | 7/2003 | Al-Ali |
| 6,993,371 B2 | 1/2006 | Kiani et al. | | 2003/0162414 A1 | 8/2003 | Schulz et al. |
| 6,993,372 B2 | 1/2006 | Fine et al. | | 2003/0171662 A1 | 9/2003 | O'Connor et al. |
| 6,996,427 B2 | 2/2006 | Ali et al. | | 2003/0176776 A1 | 9/2003 | Huiku |
| 7,003,338 B2 | 2/2006 | Weber et al. | | 2003/0181799 A1 | 9/2003 | Lindekugel et al. |
| 7,003,339 B2 | 2/2006 | Diab et al. | | 2003/0187337 A1 | 10/2003 | Tarassenko et al. |
| 7,006,855 B1 | 2/2006 | Sarussi | | 2003/0195402 A1 | 10/2003 | Fein et al. |
| 7,006,856 B2 | 2/2006 | Baker, Jr. et al. | | 2003/0197679 A1 | 10/2003 | Ali et al. |
| 7,016,715 B2 | 3/2006 | Stetson | | 2003/0212316 A1 | 11/2003 | Leiden et al. |
| 7,020,507 B2 | 3/2006 | Scharf et al. | | 2003/0225323 A1 | 12/2003 | Kiani et al. |
| 7,024,233 B2 | 4/2006 | Ali et al. | | 2003/0225337 A1 | 12/2003 | Scharf et al. |
| 7,024,235 B2 | 4/2006 | Melker et al. | | 2003/0236452 A1 | 12/2003 | Melker et al. |
| 7,025,728 B2 | 4/2006 | Ito et al. | | 2003/0236647 A1 | 12/2003 | Yoon et al. |
| 7,027,849 B2 | 4/2006 | Al-Ali et al. | | 2004/0006261 A1 | 1/2004 | Swedlow et al. |
| 7,027,850 B2 | 4/2006 | Wasserman | | 2004/0010188 A1 | 1/2004 | Wasserman et al. |
| 7,030,764 B2 * | 4/2006 | Smith et al. ............ 340/573.1 | | 2004/0024297 A1 | 2/2004 | Chen et al. |
| 7,035,697 B1 | 4/2006 | Brown | | 2004/0024326 A1 | 2/2004 | Yeo et al. |
| 7,039,449 B2 | 5/2006 | Al-Ali | | 2004/0034293 A1 | 2/2004 | Kimball |
| 7,043,289 B2 | 5/2006 | Fine et al. | | 2004/0039272 A1 | 2/2004 | Abdul-Hafiz et al. |
| 7,047,055 B2 | 5/2006 | Boaz et al. | | 2004/0039273 A1 | 2/2004 | Terry |
| 7,047,056 B2 | 5/2006 | Hannula et al. | | 2004/0054269 A1 | 3/2004 | Rantala et al. |
| 7,060,035 B2 | 6/2006 | Wasserman et al. | | 2004/0054291 A1 | 3/2004 | Schulz et al. |
| 7,062,307 B2 | 6/2006 | Norris et al. | | 2004/0059209 A1 | 3/2004 | Al-Ali et al. |
| 7,067,893 B2 | 6/2006 | Mills et al. | | 2004/0059210 A1 | 3/2004 | Stetson |
| 7,072,701 B2 | 7/2006 | Chen et al. | | 2004/0064020 A1 | 4/2004 | Diab et al. |
| 7,072,702 B2 | 7/2006 | Edgar, Jr. et al. | | 2004/0068164 A1 | 4/2004 | Diab et al. |
| 7,079,880 B2 | 7/2006 | Stetson | | 2004/0087846 A1 | 5/2004 | Wasserman |
| 7,085,597 B2 | 8/2006 | Fein et al. | | 2004/0092805 A1 | 5/2004 | Yarita |
| 7,096,052 B2 | 8/2006 | Mason et al. | | 2004/0097797 A1 | 5/2004 | Porges et al. |
| 7,096,054 B2 | 8/2006 | Abdul-Hafiz et al. | | 2004/0098009 A1 | 5/2004 | Boecker et al. |
| 7,107,088 B2 | 9/2006 | Aceti | | 2004/0107065 A1 | 6/2004 | Al-Ali et al. |
| 7,113,815 B2 | 9/2006 | O'Neil et al. | | 2004/0116788 A1 | 6/2004 | Chernoguz et al. |
| 7,123,950 B2 | 10/2006 | Mannheimer | | 2004/0116789 A1 | 6/2004 | Boaz et al. |
| 7,127,278 B2 | 10/2006 | Melker et al. | | 2004/0117891 A1 | 6/2004 | Hannula et al. |
| 7,130,671 B2 | 10/2006 | Baker, Jr. et al. | | 2004/0122300 A1 | 6/2004 | Boas et al. |
| 7,132,641 B2 | 11/2006 | Schulz et al. | | 2004/0122302 A1 | 6/2004 | Mason et al. |
| 7,133,711 B2 | 11/2006 | Chernoguz et al. | | 2004/0133087 A1 | 7/2004 | Ali et al. |
| 7,139,599 B2 | 11/2006 | Terry | | 2004/0133088 A1 | 7/2004 | Al-Ali et al. |
| 7,142,901 B2 | 11/2006 | Kiani et al. | | 2004/0138538 A1 | 7/2004 | Stetson |
| 7,162,288 B2 | 1/2007 | Nordstrom | | 2004/0138540 A1 | 7/2004 | Baker, Jr. et al. |
| 7,186,966 B2 | 3/2007 | Al-Ali | | 2004/0143172 A1 | 7/2004 | Fudge et al. |
| 7,190,987 B2 | 3/2007 | Lindekugel et al. | | 2004/0147821 A1 | 7/2004 | Al-Ali et al. |
| 7,198,778 B2 | 4/2007 | Achilefu et al. | | 2004/0147822 A1 | 7/2004 | Al-Ali et al. |
| 7,209,775 B2 | 4/2007 | Bae et al. | | 2004/0147823 A1 | 7/2004 | Kiani et al. |
| 7,215,984 B2 | 5/2007 | Diab et al. | | 2004/0147824 A1 | 7/2004 | Diab et al. |
| 7,225,006 B2 | 5/2007 | Al-Ali et al. | | 2004/0152965 A1 | 8/2004 | Diab et al. |
| 7,236,811 B2 | 6/2007 | Schmitt | | 2004/0158134 A1 | 8/2004 | Diab et al. |
| 7,248,910 B2 | 7/2007 | Li et al. | | 2004/0158135 A1 | 8/2004 | Baker, Jr. et al. |
| 7,254,433 B2 | 8/2007 | Diab et al. | | 2004/0162472 A1 | 8/2004 | Berson et al. |
| 7,254,434 B2 | 8/2007 | Schulz et al. | | 2004/0171920 A1 | 9/2004 | Mannheimer et al. |

| | | |
|---|---|---|
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0185799 A1* | 8/2005 | Bertram ................... 381/67 |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0276700 A1 | 12/2006 | O'Neil |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2008/0300471 A1 | 12/2008 | Al-Ali et al. |

FOREIGN PATENT DOCUMENTS

| | | |
|---|---|---|
| JP | 8256996 | 10/1996 |
| WO | WO 02/17780 A1 | 3/2002 |
| WO | WO 03/092576 A2 | 11/2003 |

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Belal, Suliman Yousef, et al.; "A fuzzy system for detecting distorted plethysmogram pulses in neonates and paediatric patients," *Physiol. Meas.*, vol. 22, pp. 397-412 (2001).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

* cited by examiner

METHOD AND SYSTEM FOR DETERMINING WHEN TO REPOSITION A PHYSIOLOGICAL SENSOR

BACKGROUND OF THE INVENTION

1. Field of the Invention

The present invention relates generally to medical devices and, more particularly, to the placement of sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of blood constituent in the tissue using various algorithms.

When applied to a digit or ear, it is generally desirable that the non-invasive sensor conform to the underlying tissue, fitting snugly. Such a snug fit helps exclude environmental or ambient light, which might otherwise produce incorrect or erroneous physiological data. The mild pressure associated with this snug fit, however, may be uncomfortable in some circumstances and/or may potentially compromise the accuracy of physiological measurements. Therefore, it may be desirable to reposition the sensor frequently, such as every four hours. However, doctors, nurses, and other health care providers may be unaware of the desirability to reposition the sensor frequently or may not remember when it is time to reposition the sensor.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a method for notifying an operator to reposition a sensor that includes: starting a timer upon application of a sensor to a patient, wherein the timer is set to run for a time interval; resetting the timer if the sensor is repositioned prior to the expiration of the time interval; and prompting a caregiver to reposition the sensor at the expiration of the time interval.

There is also provided one or more tangible machine-readable media that include: code adapted to start a timer upon application of a sensor to a patient, wherein the timer is set to run for a time interval; code adapted to reset the timer if the sensor is repositioned prior to the expiration of the time interval; and code adapted to prompt a caregiver to reposition the sensor at the expiration of the time interval.

There is also provided a physiological monitoring system that includes a sensor comprising at least one emitter and at least one detector; and a monitor comprising a timer set to run for a time interval and at least one of a display or speaker, wherein the timer is configured to start when the sensor is applied to a patient and to reset if the sensor is repositioned prior to the expiration of the time interval and wherein the at least one of a display or speaker is configured to provide a prompt if the sensor is not repositioned during the time interval.

There is also provided a method for starting a timer that includes: automatically determining if a sensor has been applied to a patient; and automatically starting a timer based upon a determination that the sensor has been applied to the patient.

There is also provided one or more tangible machine-readable media that include: code adapted to determine if a sensor has been applied to a patient; and code adapted to start a timer based upon a determination that the sensor has been applied to the patient.

There is also provided a physiological monitoring system that includes: a sensor comprising at least one emitter and at least one detector; and a monitor comprising a timer, wherein the timer is configured to automatically start based upon a determination that the sensor has been applied to the patient.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In pulse oximetry and other spectrophotometric applications it is desirable to monitor the time interval a sensor has been applied to a patient and to notify an operator to reposition the sensor when appropriate. In accordance with some aspects of the present technique, a system is provided that is configured to time the duration a sensor is positioned on a patient and, if the sensor is not repositioned within a given interval, to notify an operator to reposition the sensor. The duration the sensor may remain in one position on the patient may be determined by the manufacturer of the sensor and/or the monitor or may be set by the best practices and procedures of a hospital or other health care facility at which the system and sensor are employed.

Figure 1:
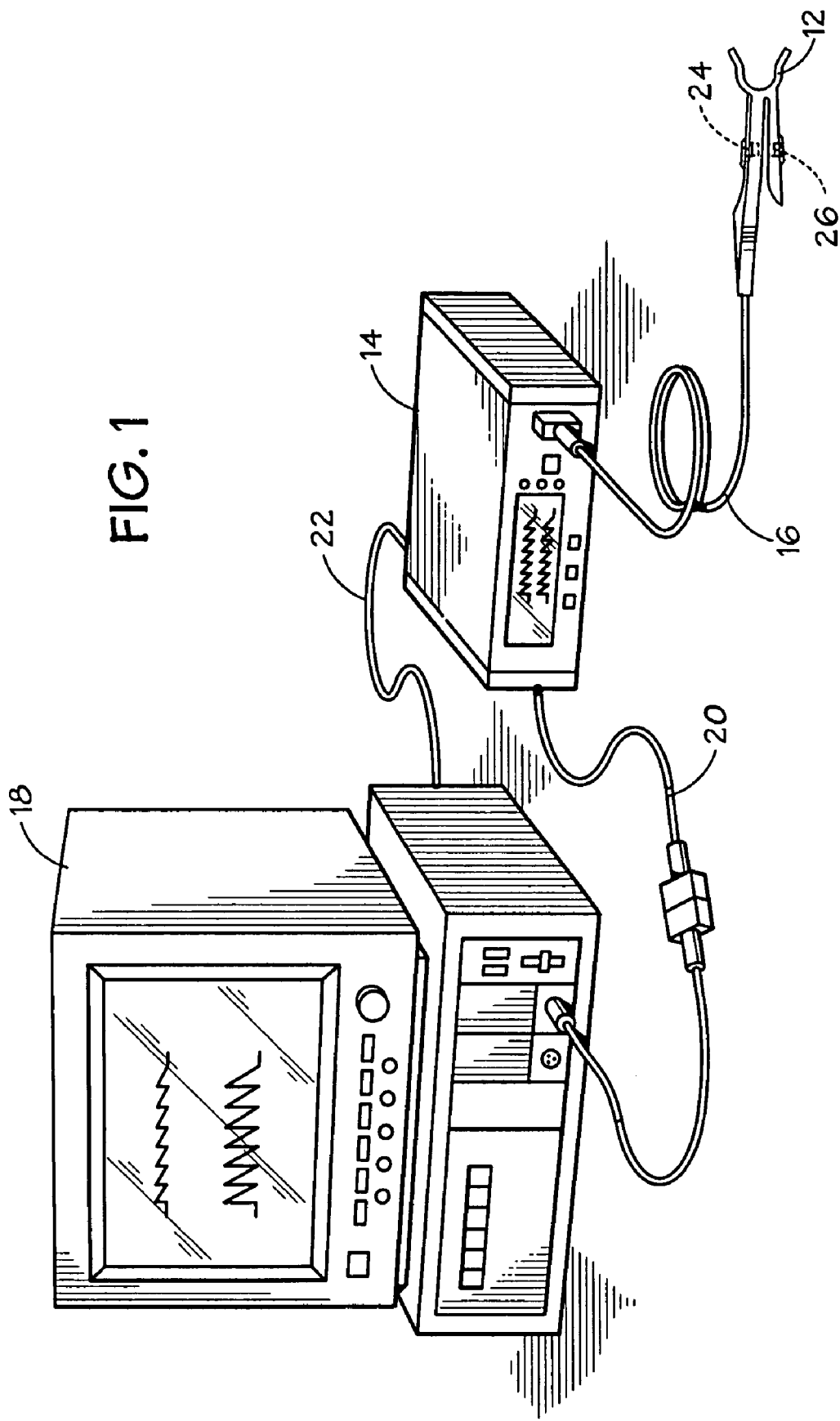
FIG. 1 illustrates a patient monitoring system coupled to a multi-parameter patient monitor and a sensor, in accordance with aspects of the present technique.

For example, referring now to FIG. 1, an exemplary patient monitoring system 10 for use in accordance with the present invention is depicted. The exemplary patient monitoring system 10 includes a sensor 12 used in conjunction with a patient monitor 14. In the depicted embodiment, a cable 16 connects the sensor 12 to the patient monitor 14. As will be appreciated by those of ordinary skill in the art, the sensor 12 and/or the cable 16 may include or incorporate one or more integrated circuit devices or electrical devices, such as a memory, processor chip, or resistor, that may facilitate or enhance communication between the sensor 12 and the patient monitor 14. Likewise the cable 16 may be an adaptor cable, with or without an integrated circuit or electrical device, for facilitating communication between the sensor 12 and various types of monitors, including older or newer versions of the patient monitor 14 or other physiological monitors. In other embodiments, the sensor 12 and the patient monitor 14 may communicate via wireless means, such as using radio, infrared, or optical signals. In such embodiments, a transmission device (not shown) may be connected to the sensor 12 to facilitate wireless transmission between the sensor 12 and the patient monitor 14. As will be appreciated by those of ordinary skill in the art, the cable 16 (or corresponding wireless transmissions) are typically used to transmit control or timing signals from the monitor 14 to the sensor 12 and/or to transmit acquired data from the sensor 12 to the monitor 14. In some embodiments, however, the cable 16 may be an optical fiber that allows optical signals to be conducted between the monitor 14 and the sensor 12.

In one embodiment, the patient monitor 14 may be a suitable pulse oximeter, such as those available from Nellcor Puritan Bennett Inc. In other embodiments, the patient monitor 14 may be a monitor suitable for measuring tissue water fractions, or other body fluid related metrics, using spectrophotometric or other techniques. Furthermore, the monitor 14 may be a multi-purpose monitor suitable for performing pulse oximetry and measurement of tissue water fraction, or other combinations of physiological and/or biochemical monitoring processes, using data acquired via the sensor 12. Furthermore, to upgrade conventional monitoring functions provided by the monitor 14 to provide additional functions, the patient monitor 14 may be coupled to a multi-parameter patient monitor 18 via a cable 20 connected to a sensor input port and/or via a cable 22 connected to a digital communication port.

As will be appreciated by those of ordinary skill in the art, the sensor 12 attached to the patient monitor 14 is typically placed on a patient in a location conducive to measurement of the desired physiological parameters. For example, a sensor 12 used for pulse oximetry is typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, or earlobes.

Where the sensor 12 is a pulse oximetry or other spectrophotometric sensor, the sensor 12 may be a "transmission type" or a "reflectance type" sensor. Transmission type sensors include an emitter 24 and detector 26 that are typically placed on opposing sides of the sensor site. Reflectance type sensors, conversely, include an emitter 24 and detector 26 that are typically placed on same side of the sensor site. During operation, the emitter 24 shines one or more wavelengths of light toward the perfused tissue. The emitted light is received by the detector 26, either on the opposite side of the tissue in transmission mode or on the same side of the tissue in reflectance mode.

The light received by the detector 26 is processed to determine various physiological characteristics of the patient. For example, in pulse oximetry, the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. In view of these example, it should be understood that, as used herein, the term "light" may refer not only to visible light, but to the electromagnetic spectrum in general, and may, therefore, include any wavelength within the infrared, ultraviolet, X-ray, gamma ray, millimeter wave, and microwave regions of the electromagnetic spectrum.

Figure 2:
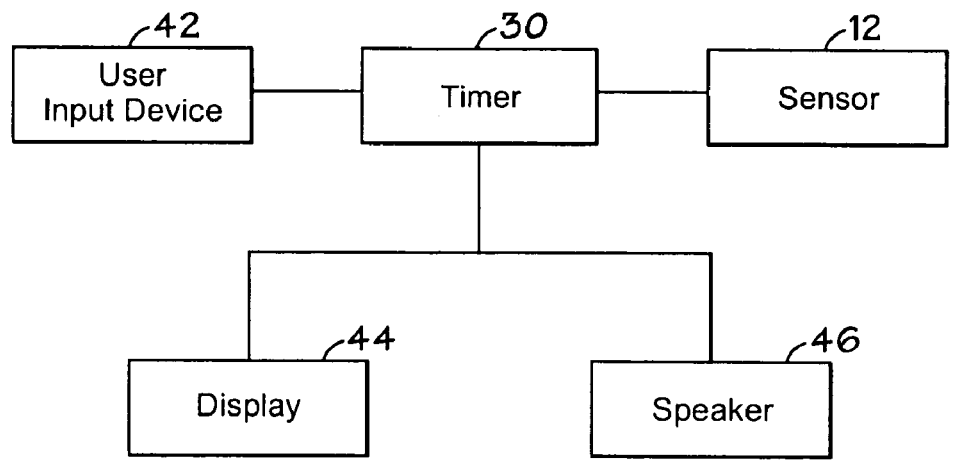
FIG. 2 illustrates components of an exemplary system for determining when to reposition a sensor, in accordance with aspects of the present technique.

As noted above, it may be desirable to routinely reposition the sensor 12 on the patient. A system and technique to facilitate the routine repositioning of the sensor 12 is discussed with regard to FIGS. 2 and 3. In particular, functional components configured to perform the operations of the present technique are depicted in FIG. 2 while exemplary operations performed in accordance with the present technique are provided in FIG. 3. As will be appreciated by those of ordinary skill in the art, the various functional components and operations of FIGS. 2 and 3 may be associated with one or more of the devices described with regard to FIG. 1. For example, to the extent that a functional component of FIG. 2 performs its function via software (such as computer implemented routines or algorithms) and/or hardware (such as general or dedicated circuitry and/or user interface devices), either the patient monitor 14 and/or the multi-parameter monitor 18 may be a suitable platform for the respective functional component. Similarly, to the extent that an operation of FIG. 3 is performed by software and/or hardware, either the patient monitor 14 and/or the multi-parameter monitor 18 may include the respective software and/or hardware to perform the operation.

Figure 3:
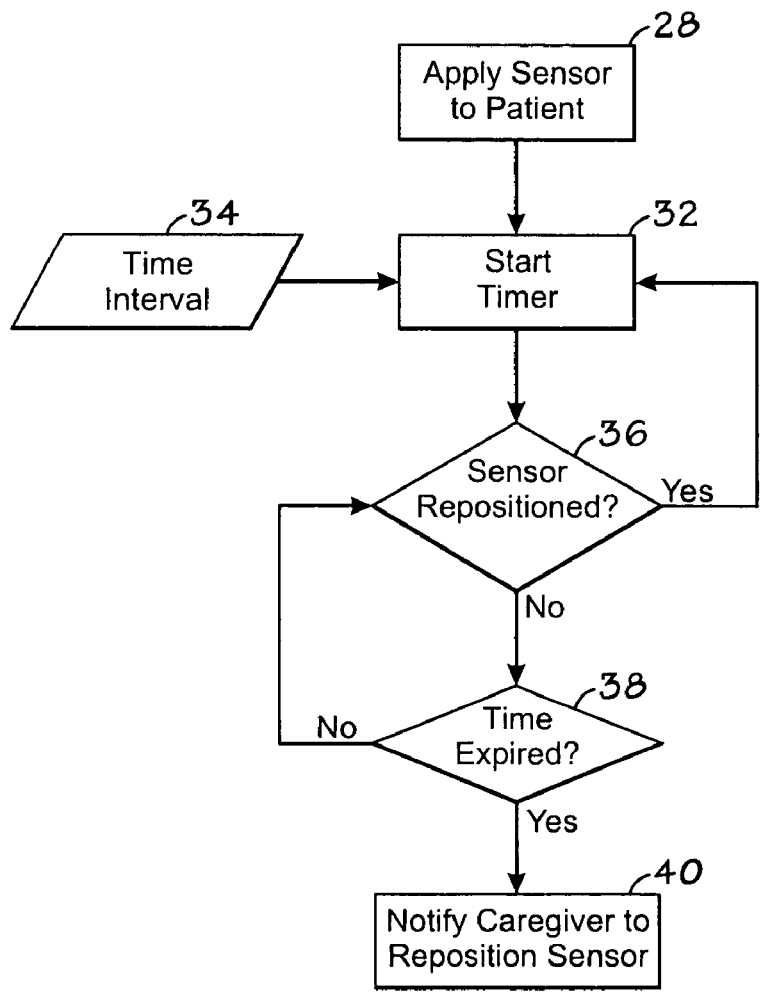
FIG. 3 is a flowchart depicting exemplary actions for determining when to reposition a sensor, in accordance with aspects of the present technique.

Referring now to FIGS. 2 and 3, a sensor 12 is applied to a patient (block 28). Upon application of the sensor 12, a timer 30 is started (block 32) which measures a set interval of time (block 34) within which the sensor 12 should be repositioned. If the sensor 12 is repositioned within the time interval 34, the timer 30 may be restarted (blocks 32 and 36). If the sensor 12 is not repositioned but the interval 34 has not yet expired, a continuing evaluation may be performed to determine if the sensor 12 is repositioned or if the interval 34 has expired (blocks 36 and 38). If, however, the sensor 12 has not been repositioned within the time interval 34 (blocks 36 and 38), a notification, such as an audible or visual indicator, may be provided to a caregiver to prompt the caregiver to reposition the sensor 12 (block 40). Upon reapplication of the sensor 12, the timer 30 may be reset and the process repeated.

As will be appreciated by those of ordinary skill in the art, the operations and functions described above may be accomplished by various means. For example, the functions of the timer 30 may be implemented by a conventional timing or timekeeping routine or algorithm, such as may be executed by processing or electronic components of the monitor 14 or 18. Alternatively, the functions of the timer 30 may be implemented by one or more dedicated circuits in the monitor 14 or 18 or by a combination of dedicated circuitry and routines. Likewise, the evaluation and notification functions described herein may also be performed by routines or algorithms executed by processing components of the monitors 14 or 18, by one or more dedicated circuits in the monitor 14 or 18, or by a combination of dedicated circuitry and routines.

With regard to the operation of the timer 30, an operator may start the timer 30 manually, such as via a user input device 42 of the monitor 14 or 18. Such a user input device 32 may include a button, dial, switch, key, or other mechanism on the monitor. Alternatively, the timer 30 may be started automatically, such as based on signals or data received from the sensor 12. In particular, a change in the light received by the detector 26 of the sensor 12 may be indicative of application of the sensor 12 to the patient and may, therefore, start the timer function. For example, a change, such as an increase or reduction, of light detected at the detector 26 may be indicative of application of the sensor 12. Such a change may be measured as a proportional change or as a change within a given unit of time. Similarly, the light detected may be evaluated in view of an absolute light threshold, with measurements on one side of the threshold indicative of an unapplied sensor and measurements on the other side of the threshold indicative of an applied sensor 12. Furthermore, only certain wavelengths of light, such as those wavelengths emitted by the emitter 24 may be used to evaluate application of the sensor 12. For example, the proportion of light received which is of the emitted wavelengths (or the relative absence of other wavelengths) may be used as an indicator of application of the sensor 12.

While light measurements are one mechanism by which sensor application may be evaluated, such as by the monitor 14 or 18, other mechanisms are also possible. For example, the receipt of valid data by the monitor 14 or 18, as determined by data evaluation routines executed by the respective monitor, may be used as an indication that the sensor 12 has been applied. Likewise, other measurements, if provided for by the sensor 12 and monitor 14 or 18 may be used to determine that the sensor 12 has been applied. For example, force or pressure sensors on the sensor 12 may be used as an indication that the sensor 12 is applied. Furthermore, other routines, algorithms, or techniques may be used to indicate whether the sensor 12 is or is not applied to the patient. For example, sensors and monitors employing neural networks and input metrics to determine a sensor ON/OFF state, as described in U.S. Pat. No. 6,035,223, hereby incorporated herein by reference, as well as other sensor ON/OFF indication techniques may be used in accordance with the present invention to indicate the application of the sensor 12 to the patient and the corresponding start of the timer 30.

The interval 34 (such as a 1, 2, or 4 hour interval) measured by the timer 30 may be set by the manufacturer of the sensor 12 or the monitor 14 or 18 based on the manufacturer's assessment of the best practices for use with their devices. For example, in one embodiment, the interval 34 is determined based upon the type of sensor 12 employed with the monitor 14. In such an embodiment, the sensor 12 or associated cable 16 may include an integrated circuit device, such as a memory device, which contains the time interval 34 itself or information (such as a model number) that may be used to ascertain the interval 34, such as via a look up table on the monitor 14.

Alternatively, the time interval 34 may be established by the hospital, clinic, or other health care facility to correspond to the facility's institutional practice or guidelines. Similarly, a supervising doctor, a nurse, or another health care provider may establish the interval 34 based on personal preference, established practice, or patient specific circumstances. In embodiments where the facility or health care provider set the interval 34, the interval 34 may be set via hardware and/or software provided on the monitor 14. For example, the interval 34 may be set by selecting the desired time interval from a menu provided on a display of the monitor 14 or by selecting the interval 34 via a user input device provided on the monitor 14.

In the event that a caregiver is to be notified to reposition the sensor 12 (block 40), the notification may be provided in various ways. For example, a visual prompt (such as a blinking light, a color coded symbol, and/or a beeping alarm) may be provided to the caregiver via a display 44 on the respective monitor. In addition, visual prompts may include alphanumeric or text messages provided on the display 44 requesting that the caregiver reposition the sensor 12. Alternatively, the routine visual indicators of the measured physiological parameter(s) may be modified to prompt the caregiver. For example, a numeric or other indicator of the measured physiological parameter may be alternated with the display of other, non-numeric characters, such as dashes, asterisks, punctuation characters, and so forth, to prompt action by the caregiver. Similarly, the numeric or other indicator of the measured physiological parameter may be displayed using a different font and/or font size than is normally used or may be displayed with emphasis, such as in italics, underlined, in bold and so forth.

Similarly the caregiver may be notified to reposition the sensor 12 (block 40) by an audible prompt provided via a speaker 46 internal or external to the respective monitor. Audible prompts may include verbal instructions or messages played on the speaker 46 in addition to or instead of displaying a visual prompt. Alternatively, the routine audible indicators generated by the respective monitor may be modified to prompt the caregiver. For example, an exemplary audible indicator may be a beep tone, such as a beep tone in which each beep corresponds to a measured pulse. Such a beep tone (or other respective audible indicator), may be modified by changing a beep characteristic (such as tone, pitch, and/or volume), by turning off the beep tone, and/or by skipping beeps, such as every second, third, or fourth beep.

Similarly, in some embodiments, the physiological data being measured, such as pulse oximetry data or tissue water fraction, may not be displayed or may be displayed in only a limited manner to notify the caregiver to reposition the sensor 12 at block 40. For example, measured physiological data, such as blood oxygen levels and/or pulse rate, may not be displayed on the monitor 14 or 18 until the sensor 12 is repositioned and the timer 30 restarted. In such embodiments, provisions may be made to display the measured physiological data in the event that the data is outside of an expected or desired range, however, routine measurements used for monitoring may be withheld to notify the caregiver that the sensor 12 should be repositioned.

In addition, the notification indicated at block 40 may be graduated or scaled based upon the extent by which the interval 34 has been exceeded. For example, a visual and/or audible prompt, such as a blinking light and/or alarm beep may be initially provided at the expiration of the interval 34 to notify the caregiver to reposition the sensor 12. If such visual and/or audible prompts do not result in the sensor 12 being repositioned, more obtrusive signals, such as brighter visual cues or louder audible indicators may be initiated until the sensor 12 is repositioned. Alternatively, if one or more rounds of visual and/or audible prompts do not result in the sensor 12 being repositioned, physiological data derived from the sensor 12 may not be provided (or may be only partially provided) to the caregiver until the sensor 12 is repositioned.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to measurements of blood oxygen saturation, but these techniques may also be utilized for the measurement and/or analysis of other blood or tissue constituents using spectrophotometric principles. For example, using the same, different, or additional wavelengths, the present techniques may be utilized for the measurement and/or analysis of carboxyhemoglobin, met-hemoglobin, total hemoglobin, intravascular dyes, and/or water content.

What is claimed is:

1. A method for notifying an operator to reposition a sensor, comprising the acts of:
   starting a timer based upon an output of a photodetector of the sensor that is indicative of the sensor being affixed to a patient, wherein the timer is set to run for a time interval;
   resetting the timer if the output of the photodetector is indicative of the sensor being removed from the patient and reaffixed to the patient prior to the expiration of the time interval; and
   prompting a caregiver to reposition the sensor at the expiration of the time interval.

2. The method of claim 1, wherein the timer is started or reset based on one or more proportional changes in the output of the photodetector that indicate the sensor has been applied or reapplied to the patient.

3. The method of claim 1, wherein the timer is started or reset based on one or more changes in the output of the photodetector within a given unit of time that indicate the sensor has been applied or reapplied to the patient.

4. The method of claim 1, wherein the timer is started or reset based on a sensor ON/OFF indication generated by a monitor in response to the output of the photodetector.

5. The method of claim 1, wherein the timer is started or reset based on one or more comparisons of the output of the photodetector with a threshold value, wherein values of the output on one side of the threshold indicate that the sensor is not applied to the patient and values of the output on the other side of the threshold indicate that the sensor is applied to the patient.

6. The method of claim 1, wherein the timer is started or reset based on a determination by one or more data evaluation routines that the output of the photodetector corresponds to valid data.

7. The method of claim 1, wherein prompting the caregiver comprises modifying a visual indicator of a physiological parameter.

8. The method of claim 7, wherein modifying the visual indicator comprises at least one of alternating a display of the parameter with non-numeric symbols, employing a different font, employing a different font size, or employing an emphasis technique.

9. The method of claim 1, wherein prompting the caregiver comprises modifying an audible indicator of a physiological parameter.

10. The method of claim 9, wherein modifying the audible indicator comprises at least one of changing the tone of an audible indicator, turning the audible indicator off, periodically skipping the audible indicator.

11. The method of claim 9, wherein the audible indicator is a beep tone.

12. The method of claim 1, wherein prompting the caregiver comprises providing at least an audible prompt.

13. The method of claim 12, wherein the audible prompt comprises an audible alarm or a verbal message.

14. The method of claim 1, wherein prompting the caregiver comprises not displaying at least one physiological parameter derived from data acquired by the sensor.

15. One or more tangible machine-readable media comprising:
   code adapted to start a timer based upon an output of a photodetector of a sensor that is indicative of the sensor being affixed to a patient, wherein the timer is set to run for a time interval;
   code adapted to reset the timer if the output of the photodetector indicates that the sensor was removed and reaffixed to the patient prior to the expiration of the time interval; and
   code adapted to prompt a caregiver to reposition the sensor at the expiration of the time interval.

16. The one or more tangible machine-readable media of claim 15, wherein the code adapted to start or reset the timer starts or resets the timer based on one or more proportional changes in the output of the photodetector that indicate the sensor has been applied or reapplied to the patient.

17. The one or more tangible machine-readable media of claim 15, wherein the code adapted to start or reset the timer starts or resets the timer based on one or more changes in the output of the photodetector within a given unit of time that indicate the sensor has been applied or reapplied to the patient.

18. The one or more tangible machine-readable media of claim 15, wherein the code adapted to start or reset the timer starts or resets the timer based on a sensor ON/OFF indication generated by a monitor in response to the output of the photodetector.

19. The one or more tangible machine-readable media of claim 15, wherein the code adapted to prompt the caregiver provides at least a visual prompt.

20. The one or more tangible machine-readable media of claim 19, wherein the visual prompt comprises a blinking light, an alphanumeric message, or a color code.

21. The one or more tangible machine-readable media of claim 15, wherein the code adapted to prompt the caregiver modifies a visual indicator of a physiological parameter.

22. The one or more tangible machine-readable media of claim 21, wherein modifying the visual indicator comprises at least one of alternating a display of the parameter with non-numeric symbols, employing a different font, employing a different font size, or employing an emphasis technique.

23. The one or more tangible machine-readable media of claim 15, wherein the code adapted to prompt the caregiver modifies an audible indicator of a physiological parameter.

24. The one or more tangible machine-readable media of claim 23, wherein modifying the audible indicator comprises at least one of changing the tone of an audible indicator, turning the audible indicator off, periodically skipping the audible indicator.

25. The one or more tangible machine-readable media of claim 23, wherein audible indicator is a beep tone.

26. The one or more tangible machine-readable media of claim 15, wherein the code adapted to prompt the caregiver provides at least an audible prompt.

27. The one or more tangible machine-readable media of claim 26, wherein the audible prompt comprises an audible alarm or a verbal message.

28. The one or more tangible machine-readable media of claim 15, wherein the code adapted to prompt the caregiver does not display at least one physiological parameter derived from data acquired by the sensor.

29. A method of using a sensor, the method comprising the acts of:
   starting a timer upon a sensor being affixed to the skin of a patient, wherein the timer is set to run for a time interval;
   determining whether the sensor is repositioned based upon a change in the amount of light detected by a photodetector of the sensor;
   resetting the timer if the sensor is repositioned prior to the expiration of the time interval; and
   prompting a caregiver to reposition the sensor at the expiration of the time interval.

30. The method of claim 29, wherein starting the timer comprises starting the timer based upon an initial change in the amount of light detected by the photodetector.

31. The method of claim 29, wherein determining whether the sensor is repositioned comprises one or more of assessing the proportion of the change in the amount of light, assessing the time interval over which the change occurs, or comparing the amount of light detected after the change to a threshold value.

32. The method of claim 29, wherein prompting the caregiver comprises modifying a visual indicator of a physiological parameter.

33. The method of claim 29, wherein prompting the caregiver comprises modifying an audible indicator of a physiological parameter.

34. The method of claim 29, wherein prompting the caregiver comprises not displaying at least one physiological parameter derived from data acquired by the sensor.

35. A method of using a sensor, the method comprising the acts of:
   starting a timer upon a sensor being affixed to a patient;
   determining whether the sensor is repositioned based upon one or more comparisons of the amount of light detected by a photodetector of the sensor to a threshold value, wherein the amount of light detected crossing and recrossing the threshold is indicative of the sensor being repositioned;
   resetting the timer if the sensor is repositioned prior to the timer reaching a time limit; and
   prompting a caregiver to reposition the sensor if the timer reaches the time limit.

36. The method of claim 35, wherein starting the timer comprises starting the timer based on the amount of light detected by the photodetector crossing the threshold value.

37. The method of claim 35, wherein the threshold comprises an absolute light threshold.

38. The method of claim 35, wherein prompting the caregiver comprises modifying a visual indicator of a physiological parameter.

39. The method of claim 35, wherein prompting the caregiver comprises modifying an audible indicator of a physiological parameter.

40. The method of claim 35, wherein prompting the caregiver comprises not displaying at least one physiological parameter derived from data acquired by the sensor.

41. A method of using a sensor, the method comprising the acts of:
   starting a timer upon a sensor being affixed to a patient;
   determining whether the sensor is repositioned based upon an algorithm executed on a monitor in communication with the sensor, wherein the algorithm indicates whether the sensor is currently on or off;
   resetting the timer if the sensor is repositioned prior to the timer reaching a time limit; and
   prompting a caregiver to reposition the sensor if the timer reaches the time limit.

42. The method of claim 41, wherein starting the timer comprises starting the timer based on an indication generated by the algorithm that the sensor is on.

43. The method of claim 41, wherein the algorithm employs one or more of neural networks or input metrics to determine the on or off state of the sensor.

44. The method of claim 41, wherein prompting the caregiver comprises modifying a visual indicator of a physiological parameter.

45. The method of claim 41, wherein prompting the caregiver comprises modifying an audible indicator of a physiological parameter.

46. The method of claim 41, wherein prompting the caregiver comprises not displaying at least one physiological parameter derived from data acquired by the sensor.

47. One or more tangible machine-readable media comprising:
   code adapted to start a timer upon application of a sensor to a patient;
   code adapted to determine whether the sensor is repositioned based upon a change in the amount of light detected by a photodetector of the sensor;
   code adapted to reset the timer if the sensor is repositioned prior to the timer reaching a time limit; and
   code adapted to prompt a caregiver to reposition the sensor if the timer reaches the time limit.

48. The one or more tangible machine-readable media of claim 47, wherein the code adapted to start the timer starts the timer based upon an initial change in the amount of light detected by the photodetector.

49. The one or more tangible machine-readable media of claim 47, wherein the code adapted to determine whether the sensor is repositioned performs one or more of assessing the proportion of the change in the amount of light, assessing the time interval over which the change occurs, or comparing the amount of light detected after the change to a threshold value.

50. The one or more tangible machine-readable media of claim 47, wherein the code adapted to determine whether the sensor is repositioned comprises an algorithm embodied on the tangible machine readable media and executable by a patient monitor, wherein the algorithm, when executed, indicates whether the sensor is currently on or off.

51. The one or more tangible machine-readable media of claim 47, wherein the code adapted to prompt the caregiver modifies a visual indicator of a physiological parameter.

52. The one or more tangible machine-readable media of claim 47, wherein the code adapted to prompt the caregiver modifies an audible indicator of a physiological parameter.

* * * * *